United States Patent
Millar et al.

(10) Patent No.: US 11,026,574 B2
(45) Date of Patent: Jun. 8, 2021

(54) APPARATUS AND METHOD FOR USING INFRARED THERMOGRAPHY FOR VIEWING A TEAR FILM

(71) Applicant: BEYOND 700 PTY LTD, Castle Hill (AU)

(72) Inventors: Thomas Millar, Castle Hill (AU); Burkhardt Siegfried Schuett, Castle Hill (AU)

(73) Assignee: BEYOND 700 PTY LTD, Castle Hill (AU)

( * ) Notice: Subject to any disclaimer, the term of this patent is extended or adjusted under 35 U.S.C. 154(b) by 41 days.

(21) Appl. No.: 16/308,150

(22) PCT Filed: Jun. 8, 2017

(86) PCT No.: PCT/AU2017/050575
§ 371 (c)(1),
(2) Date: Dec. 7, 2018

(87) PCT Pub. No.: WO2017/210746
PCT Pub. Date: Dec. 14, 2017

(65) Prior Publication Data
US 2019/0175012 A1 Jun. 13, 2019

(30) Foreign Application Priority Data

Jun. 8, 2016 (AU) .................................. 2016203805

(51) Int. Cl.
*A61B 3/10* (2006.01)
*A61B 3/14* (2006.01)
(Continued)

(52) U.S. Cl.
CPC ............ *A61B 3/101* (2013.01); *A61B 3/0083* (2013.01); *A61B 3/10* (2013.01); *A61B 3/14* (2013.01); *A61B 5/015* (2013.01); *A61B 5/14507* (2013.01)

(58) Field of Classification Search
CPC ......... A61B 3/101; A61B 3/0083; A61B 3/10; A61B 3/14; A61B 5/015; A61B 5/14507; H04N 5/33; H04N 5/332
(Continued)

(56) References Cited

U.S. PATENT DOCUMENTS 8,909,327 B1 * 12/2014 Bosworth .............. A61B 3/103
600/473
2006/0232674 A1 * 10/2006 Cochran ................... H04N 5/33
348/164
(Continued)

OTHER PUBLICATIONS

Millar et al. "The real reason for having a meibomian lipid layer covering the outer surface of the tear film—A review." Experimental Eye Research. vol. 137, pp. 125-138 and accompanying "Graphical Abstract"). Retrieved from the internet on Jun. 6, 2017 <URL: http://www.sciencedirect.com/science/article/pii/S001448351500144X> published online May 14, 2015.
(Continued)

*Primary Examiner* — Jordan M Schwartz
(74) *Attorney, Agent, or Firm* — Procopio, Cory, Hargreaves & Savitch LLP

(57) ABSTRACT

Disclosed is an apparatus for observing a tear film on a persons or animals eye. The apparatus comprises an infrared sensitive camera that includes a camera lens system and a computer configured to receive data from the camera, process the data using software and represent the processed data on a display. The camera is configured to measure temporal and spatial changes of thermal radiation from a surface of the eye at a frame rate, a spatial resolution, and a thermal
(Continued)

sensitivity that allows the dynamics of the tear film to be visualised. Also disclosed is a method of observing a tear film on an eye of a person or an animal using an apparatus, such as that described above, where the method includes the step of viewing the dynamics of the tear film using the apparatus.

20 Claims, 7 Drawing Sheets

(51) Int. Cl.
      *A61B 5/01*       (2006.01)
      *A61B 5/145*     (2006.01)
      *A61B 3/00*       (2006.01)

(58) Field of Classification Search
    USPC .......... 351/206, 210; 250/330, 332; 359/356
    See application file for complete search history.

(56) References Cited

U.S. PATENT DOCUMENTS

2008/0174733 A1     7/2008   Chang et al.
2010/0201944 A1*   8/2010   Lewis .................. G06T 7/0012
                                                  351/206
2012/0057126 A1     3/2012   Chang et al.
2013/0010257 A1*   1/2013   Primeau ................... A61B 3/14
                                                    351/205
2013/0079660 A1     3/2013   Chang et al.
2018/0092534 A1*   4/2018   Nabhan ................ A61B 3/0041

OTHER PUBLICATIONS

Abreau et al. "Temperatures of the Ocular Surface, Lid, and Periorbital Regions of Sjogren's, Evaporative, and Aqueous-Deficient Dry Eyes Relative to Normals." The Ocular Surface. 14(1):64-73 (Jan. 2016).

Wing et al. "Ocular Surface Cooling Corresponds to Tear Film Thinning and Breakup." Optometry and Vision Science. 92(9):e248-e256 (Sep. 2015).

International Search Report and Written Opinion for corresponding PCT application No. PCT/AU2017/050575, dated Aug. 21, 2017, in 9 pages.

\* cited by examiner

APPARATUS AND METHOD FOR USING INFRARED THERMOGRAPHY FOR VIEWING A TEAR FILM

TECHNICAL FIELD

The herein described apparatus and method relate to the direct imaging and visualisation of the dynamics of a tear film. This may include, but is not limited to, visualising the stability and integrity of a tear film during and after a blink in mammals, for example.

PREVIOUS APPLICATION DATA

The present application claims priority from Australian Patent Application No. 2016203805, the contents of which are hereby incorporated in their entirety.

BACKGROUND

The tear film covering the ocular surface of mammalian eyes is composed of three components: a mucin component; an aqueous component containing salts, proteins and nutrients; and a lipid component (Holly and Lemp 1977 Surv Ophthalmol 22:69-87; Chen et al 1997 Invest Ophthalmol Vis Sci 38:381-387). All components are important for the protection and lubrication of the corneal surface during blink processes as well as for water retention while the eye is exposed to the air when it is open.

The performance of the tear film can be altered by disease, poor or incomplete blinking patterns, ocular surgery, physiological changes, and insertion of devices onto or into the ocular surface. An underperforming tear film can present clinically in one or a number of symptoms such as redness, itchiness, burning, grittiness, and irritation, which can lead to ocular discomfort, pain and ultimately damage to the cornea. However, some of these symptoms could be due to different causes and so it is essential for diagnosis to have an indication of tear film performance.

Currently it is not possible to directly visualise the natural tear film and it is problematic to measure alterations to it. Consequently, current techniques focus on measuring parameters associated with a common endpoint for a poor performing tear film. This endpoint is referred to as dry eye syndrome or keratoconjunctivitis sicca (Pflugfelder et al 2000 Cornea 19:644-649; Jester (ed) 2004 Ocular Surface 2:53-168). These surrogate measures for evaluating the performance of the tear film are further limited in that for any particular parameter used to evaluate dry eye, there is no common threshold and often the thresholds vary between practitioners. A practitioner therefore typically uses a number of different surrogate measures to evaluate the tear film in the context of dry eye.

At present, a recommendation for best clinical practice is a sequence of tests for the diagnosis of dry eye. This involves: an initial patient history; a general eye examination; a validated symptom questionnaire; and at least two objective tests to measure the status of the tear film, ocular surface, or meibomian glands (Pflugfelder et al 2000 Cornea 19:644-649; Jester (ed) 2004 Ocular Surface 2:53-168; Sweeney et al 2013 Exp Eye Res 117:28-38).

Questionnaires rely on subjective views and scaling by the patient, and so signs of dry eye are measured by objective tests. At best, these tests have a predictive value of ~70%. Most of these tests are invasive and so the tear film is affected by doing the tests. Tear break-up time involves putting fluorescein into the tear film. Measuring tear volume involves placing filter strips (Schirmer tests) or cotton threads (phenol red thread tests) in the eye. Measuring osmolarity (an indicator of excessive evaporation of the tears) involves collecting tears. To test for meibomian gland dysfunction, the glands are manually expressed, and the results are of variable diagnostic use.

Therefore, evaluation of the performance and stability of the tear film is indirect, costly and time consuming because it requires multiple diagnostic methods. It is vexing because it is difficult to correlate the results to symptoms described by the patients. Therefore, there is currently no holistic direct measurement or observation that can be used to evaluate the dynamic performance of the tear film. Thus currently, any diagnosis that relates to tear film performance relies on a culmination of tests and a most likely probability.

The reference in this specification to any prior publication (or information derived from it), or to any matter which is known, is not, and should not be taken as, an acknowledgement or admission or any form of suggestion that prior publication (or information derived from it) or known matter forms part of the common general knowledge in the field of endeavour to which this specification relates.

SUMMARY

In view of the forgoing, the present invention seeks to overcome the drawbacks of prior methods for studying tear film performance. In particular, the present invention seeks to provide a method to directly visualise the natural tear film without interfering with the tear film itself. Furthermore, the present invention seeks to provide a method for direct visual discrimination of a healthy tear film from an abnormal tear film. Finally, the present invention seeks to provide a method to directly visualise the effects of treatments on the performance of the tear film without interfering with the treatment.

The invention described herein pertains to using ocular surface thermography to visualise the dynamic tear film in real time. According to one aspect of the invention, there is provided an apparatus for observing a tear film on a person's or animal's eye, the apparatus comprising: an infrared sensitive camera that includes a camera lens system; and a computer configured to receive data from the camera, process the data using software and represent the processed data on a display, wherein the camera is configured to measure temporal and spatial changes of thermal radiation from a surface of the eye at a frame rate, a spatial resolution, and a thermal sensitivity that allows the dynamics of the tear film to be visualised.

In one form, the apparatus further comprises a frame including an adjustable chin rest, wherein the camera is mounted to the frame. In another form, the camera is hand held.

In other non-limiting example forms: the dynamics of the tear film are visualised during and after a blink; and/or a recording device records the data from the camera. In some example forms, the data on the display allows a region of the eye on which the tear film has reformed following a blink can be distinguished from a region where this has not occurred.

In other example forms: the camera includes a detector for wavelengths in the bands from 2 micrometres to 14 micrometres; the camera includes a detector for wavelengths only in the bands from 8 micrometre to 14 micrometres; and the camera includes a detector for wavelengths only in the bands from 1.5 micrometres to 5.1 micrometres. In yet other example forms: the frame rate is at least 25 frames per second; the frame rate is at least 60 frames per second; and the frame rate is at least 100 frames per second. In yet other example forms: the camera includes a detector that captures at least 320×240 pixels; and the camera includes a detector that captures at least 640×512 pixels. In yet other example forms: the camera includes a detector with a pitch resolution of 17 micrometres or less; and the camera includes a detector with a pitch resolution of 15 micrometres or less. In yet other example forms: the thermal sensitivity is at least 20 milliKelvin; and the thermal sensitivity is at least 15 milliKelvin.

According to another aspect of the invention, there is provided a method of observing a tear film on an eye of a person or an animal using an apparatus comprising an infrared sensitive camera that includes a camera lens system, the camera being configured to measure temporal and spatial changes of thermal radiation from a surface of the eye at a frame rate, a spatial resolution, and a thermal sensitivity that allows the dynamics of the tear film to be visualised, wherein the method includes the step of viewing the dynamics of the tear film using the apparatus.

In other non-limiting example forms, the method further includes the step of visualising a tear film abnormality in the eye that is caused by: an abnormal spreading of the tear film; and/or an abnormal stability of the tear film. In yet other non-limiting example forms, the method further includes the step of visualising a change to the tear film in the eye that is caused by: wearing a contact lens or other ocular device; a previous ocular surgery; an altered physiological or pathological state of the eye surface; a treatment of the eye; and/or a different blinking regime. In one form, the dynamics of the tear film are viewed during and after a blink.

According to another aspect of the invention, there is provided a method of viewing an eye of a person or an animal, the method including the step of: viewing the eye using an apparatus substantially as defined herein; and detecting a lack of tear film in the eye.

The above methods can be used to diagnose an ocular situation where the performance of the tear film could be altered, and to monitor the impact of treatment on the tear film. One such condition is dry eye syndrome and this technique may be suitable to distinguish between different types of dry eye including lipid deficiency, mucin deficiency, aqueous deficiency and deficiency of excretion of lipids from meibomian gland orifices, which can all be related to dry eye.

Furthermore, this technique may allow monitoring of the performance of the tear film of subjects where there is a possibility for aberrant spread of the tear film. Such conditions include, but are not confined to, subjects with poor or incomplete blinking patterns, subjects having undergone ocular surgical procedures such as refractive surgery and keratoplasty, subjects wearing ocular devices such as contact lenses, and subjects with ocular conditions such as, but not confined to, keratoconus, ocular allergies, blepharitis, Sjögren's syndrome and shingles.

Furthermore, this technique may be suitable for monitoring treatments affecting the tear film. Such treatments include but are not limited to eye drops, eye plugs, any medication or treatment affecting the tear composition, and treatments stimulating meibum secretion.

Prior to the present invention, there was no method available for directly observing the dynamics of a natural tear film during and after a blink. Such a visualisation is useful for assessment of ocular health.

The method described herein is the use of thermography for visualising the natural tear film dynamics during a blink and after a blink. This method can be used to visualise a subject's ocular tear film. This imaging of the tear film can be used for the evaluation of a subject's tear film performance and can therefore be used for: the diagnosis of dry eye; determining the effect of varying the type of blinking on the tear film; determining the effects of poor or incomplete blinking patterns on the tear film; the monitoring of performance of the tear film following ocular surgery; the evaluation of the tear film in ocular disease or altered physiological states; evaluating changes to the tear film after applying devices to the ocular surface; determining the effects of eye drops or other treatments on the performance of the tear film and hence their effectiveness as treatment for ocular conditions.

In this regard, embodiments disclosed herein include an infrared sensitive camera that is used to film the ocular surface. Such a camera needs to have appropriate wavelength sensitivity, minimal spatial resolution, thermal sensitivity and a frame rate necessary to capture the dynamics of the blink. The camera is attached to a computer and monitor, and software installed on the computer is used to process the video data gathered by the camera.

In essence, the camera captures the thermal radiation from the surface of the eye. By doing this with an adequate frame rate, wavelength, thermal and spatial resolution, the spread of the tear film over the surface of the eye during a blink as well as the performance of that film while the eye is kept open can be visualised.

Advantageous Effects of the Invention

During and after a blink and initial spreading, the infrared sensitive camera can monitor thermal radiation changes of the ocular surface as the eye opens and from the open eye. Dynamic changes to local regions of the natural tear film can be observed in real time and in particular, regions of decreased thermal radiation during this process are attributed to evaporative cooling of the surface. This differs from previous applications of thermography of the ocular surface, where evaporative cooling over the entire eye or a defined region was measured or calculated. These applications of thermography were successful in showing that temperature changes in dry eye subjects are different to normal control subjects, but none of the methods demonstrated or evaluated the actual blink and tear film dynamics. The present invention also differs from techniques that measure tear film stability by applying a fluorophore to the tear film in that it measures the natural tear film without addition of detector chemicals.

The invention described herein allows an observer immediate visual discrimination between a healthy natural tear film that spreads completely over the ocular surface and remains stable over time from an abnormal tear film. It also allows: observation of the effects of normal versus forceful blinks on the tear film; discrimination between different types of abnormal tear films; and changes to the tear film by carrying out procedures/treatments that affect the tear film. For experts familiar in the art, it is obvious that this method is the first method that enables direct visualisation of the natural tear film and hence allows an easy direct diagnosis of tear film abnormalities.

BRIEF DESCRIPTION OF THE DRAWINGS

Example embodiments should become apparent from the following description, which is given by way of example only, of at least one preferred but non-limiting embodiment, described in connection with the accompanying figures, wherein.

DESCRIPTION OF EMBODIMENTS

Figure 1:
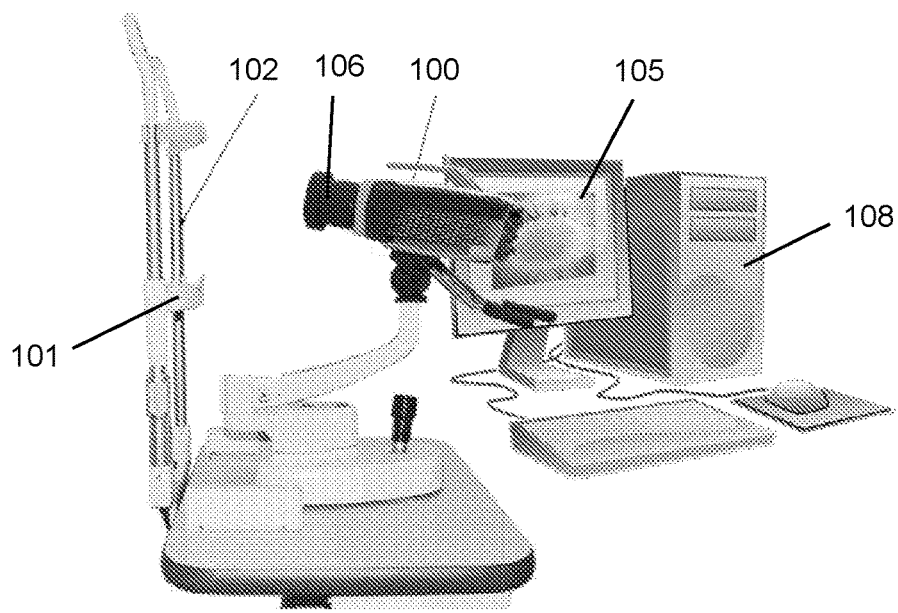
FIG. 1 is a schematic view of using an infrared thermal imager to observe a tear film in accordance with the present invention.

The following modes, given by way of example only, are described in order to provide a more precise understanding of the subject matter of a preferred embodiment or embodiments.

In the Figures, incorporated to illustrate features of an example embodiment, like reference numerals are used to identify like parts throughout the Figures.

In the embodiment as shown in FIG. 1, an apparatus called herein a "tear film thermographer" comprises a movable infrared sensitive camera 100 and a chin rest 101 adjustably mounted on a frame 102. A thermographic film of the eye's surface can be taken by that camera 100 and a digital interpretation of the image presented on a display 105.

It will be appreciated that while the present embodiment uses a frame 102 to support the camera 100 and a chin rest 101 on which the subject places their head for support during a procedure, alternative embodiments may use a camera 100 that can be hand held, may be configured to slot into an existing slit lamp, or be supported in any other suitable manner. Such a flexible device may be beneficial in circumstances where a more portable device is required, or for viewing the eyes of animals other than humans, for example.

The area of interest to be filmed will be an open eye's surface. The invention is primarily directed to use with human eyes, however it is also suitable to be used for filming the eyes of other animals. Thus, to have maximal resolution a suitable optic, or camera lens system 106, is mounted to the camera 100 to be able to focus and maximise on the desired area of an eye reaching an infrared sensitive chip within the camera.

Such films can also be taken from both eyes simultaneously, but in this case resolution will be lost and depending on the quality of the camera the number of pixels making up the picture of the eye's surface are reduced and the necessary detailed thermographic film cannot be taken. Accordingly, the description of this invention should be understood as a broad description taking into account either sequential or simultaneous measurement of the eyes of subjects.

The camera 100 is mounted to the frame 102 in a manner that allows sufficient freedom to be moved and also angled as necessary to film the eye. A computer 108 is configured to receive data from the camera 100, process the data and represent the processed data on the display 105.

The camera 100 is configured to measure temporal and spatial changes of thermal radiation of the surface of the eye at a frame rate, a spatial resolution, and a thermal sensitivity that allows the dynamics of the tear film to be visualised. For example, the embodiment of FIG. 1 uses an infrared sensitive camera 100 with a detector for wavelengths in the bands from 2 micrometres to 14 micrometres (μm), sensing 640× 512 pixels, having a thermal sensitivity of 20 milliKelvin (mK) and running at a minimum of 25 frames per second (Hz) to detect the tear film and changes in the tear film over time.

The photodetector can be cooled and of different materials which include, but are not limited to, indium antimonide, indium arsenide, platinum silicide and mercury cadmium telluride. A common cooling mechanism that would be used is a Stirling engine cryocooler, but others such as gas coolers and LN2 Dewer could also be used. The photodetectors include high band gap semiconductors such as quantum well infrared photodetectors. The digital information from the camera is processed by appropriate software being run by the computer 106.

Uncooled thermal cameras with detectors that have the necessary thermal sensitivity could also be used. Such devices have sensors that change the resistance, voltage or current when heated by infrared radiation. Examples of these are microbolometers and devices that are based on pyroelectric and ferroelectric materials.

An example of the technology used to view the dynamics of the tear film is a Stirling engine cryocooled camera running at a frame rate of 100 Hz using an indium antimonide sensor with 640×512 pixels, with a pitch resolution of 15 µm, a 1.5-5.1 µm spectral response and a thermal sensitivity of 15 mK, equipped with a 50 mm lens and a 20 mm extension ring.

Another example of the technology used to view the dynamics of the tear film is an uncooled microbolometer running at a frame rate of 60 Hz in a temperature window of 20° C.-40° C. using a vanadium oxide sensor with 320×240 pixels, a pitch resolution of 17 µm, a 8-14 µm spectral response, a thermal sensitivity of 20 mK and equipped with a 7.5 mm lens.

For the purpose of real time data visualisation, data transfer and data storage of the data representing the video output signals of the camera 100, a computer system 108 is used. A camera 100 with an internal storage buffer can also be used.

For viewing the motion of the tear film and the dynamics of the blink, about 25 frames per second are just satisfactory, however higher frame rates are desirable. For example, other embodiments may use a frame rate of 30 Hz, 40 Hz, 50 Hz, or even 100 Hz or higher.

Software to run the camera, capture the films, retrieve and store the films is an integral part of this system (FIG. 1). Recording may be performed by a recording device that forms part of the computer 108 or is implemented by the software, a recording device the is associated with the camera 100 or any other suitable recording device as would be known to those skilled in the art.

A typical eye examination session proceeds as follows: The camera system is started and if necessary the camera 100 is cooled to operational requirements. The computer 108 and the necessary software are started. The patient is seated in front of the camera 100 and asked to place his/her chin in the chin rest 101. The chin rest 101 is adjusted for the patient to sit comfortably.

The camera 100 is adjusted to place it horizontally in front of the eye of the patient. The camera 100 can either work with a fixed focus or an adjustable focus. In the case of a fixed focus, the camera 100 is moved on the horizontal axis to or away from the eye of the patient to get the thermographic picture in focus. If the focus of the camera 100 is not fixed, additional adjustments can be made using the focal lens of the camera 100.

After the eye is in focus of the camera 100, the operator of the tear film thermographer gives instructions to the patient for blinking regimes and films are taken and recorded as desired.

The system can be fully motorized, manual, semi-autonomous or autonomous in operation. Such a tear film thermographer could be a stand-alone system or attached to another ophthalmic instrument allowing for movement of the camera 100 into the right position in front of the eye of a patient. Such a system could be a slit lamp to which an infrared sensitive camera is attached so it can be moved as required.

EXAMPLES

Extensive research has established what happens to the tear film during the blink and after the blink as observed with the dynamic thermography using a tear film thermographer as disclosed herein. All thermographs shown in FIGS. 2-15 are scaled in grey, where darker grey represents less thermal radiation. Changes in emissivity of the surface are observed and these emissivity changes may be attributed to the lipid layer density changes of the tear film while the tear film is spreading and can also be observed during and after these lipids have been released from the meibomian glands of the lower eye lids.

It is known that during the eyelid closing phase of a blink cycle some aqueous is removed and it is replenished during eyelid opening (Sorbara et al 2004 Contact Lens Ant Eye 27:15-20; Khanal and Millar 2010 Nanomedicine. 6:707-713). For a normal natural tear film, at the beginning of the eye opening phase of a blink, a darker narrow front across the ocular surface (Feature F1; in FIGS. 2-4, 6-8, 10-15), which moves from the lower eyelid towards the upper eyelid, can be seen. Being darker, this front appears to emit less thermal radiation and has lower emissivity than the surface of the eye it is spreading over. This may be in part related to the emissivity changes due to the lipid layer forming on the top of the tear film and in part related to the aqueous component of the tear film evaporating.

Figure 2:
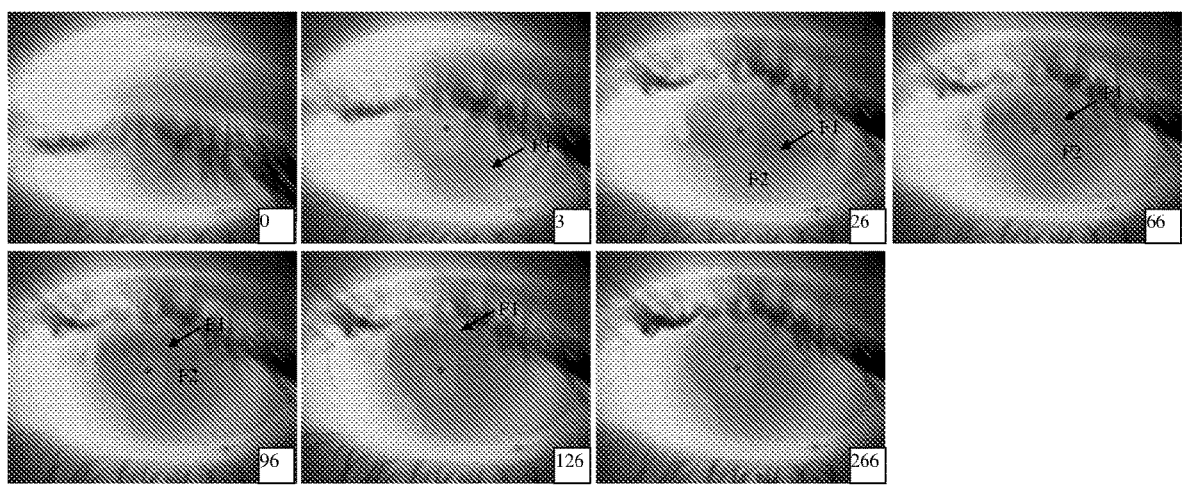
FIG. 2 shows a series of thermographs (from a thermographic movie; the numbers represent time periods of 0.01 s after the blink) showing the moving tear film of a normal subject's eye following a blink.

Following behind this dark front is a light grey region (Feature F2 in FIGS. 2, 3, 6, 10, 11, 14, 15) representing a newly formed complete tear film covering the ocular surface. Research has identified that the dark front is indicative of an aqueous component of the tear film that has not fully integrated in the tear film during its spread after opening the eye. It also represents changes in emissivity of the tear film due to the lipid front moving simultaneously. Since this part of the aqueous of the tear film is not fully integrated into the tear film it can evaporate, hence the small difference in thermal radiation compared to the surface of the eye the film has already spread over. Again, research has shown that in healthy subjects not affected by dry eye or other problems to the tear film, this front (Feature F1) moves up over the ocular surface and then disappears at the upper eye margin (FIG. 2).

The spreading front of the tear film (Feature F1) can be fast moving (within a tenth of a second from opening the eye until it reaches the top of the eye) or relatively slow (the same process over a second or more). These different velocities are due to differences of interaction of the aqueous component and lipid component of the tear film with the mucinious component of the tear film. Following behind this front in a normal healthy eye is the complete tear film (Feature F2 in FIG. 2). Also in healthy subjects, the resulting complete film does not show a substantial drop in thermal radiation over time (not becoming darker while the eye is open indicating a stable non-evaporative tear film; FIG. 2).

Figure 3:
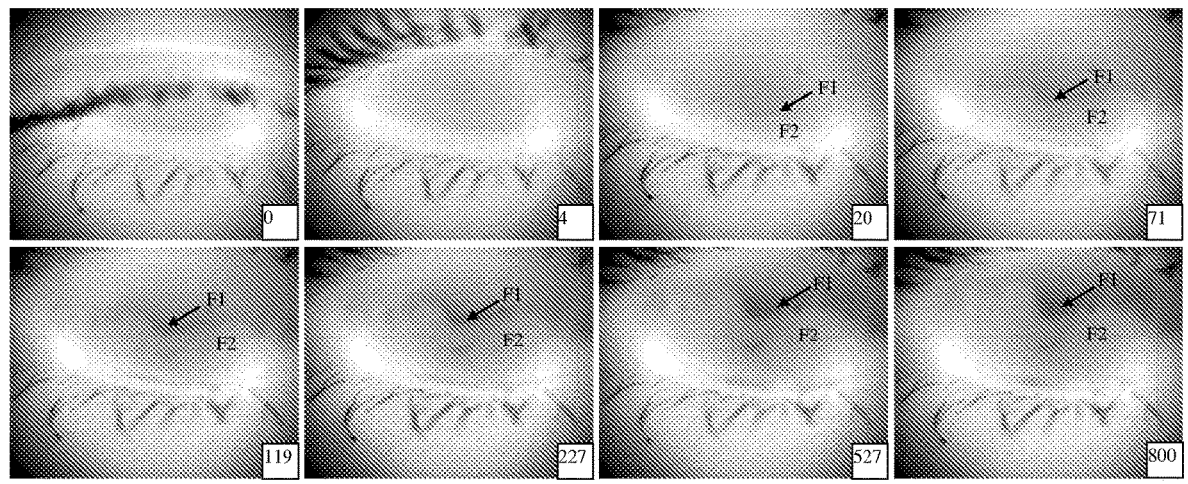
FIG. 3 shows a series of thermographs (from a thermographic movie; the numbers represent time periods of 0.01 s after the blink) of a subject's eye, who had been diagnosed with dry eye, with incomplete spreading of the tear film following a blink.
Figure 4:
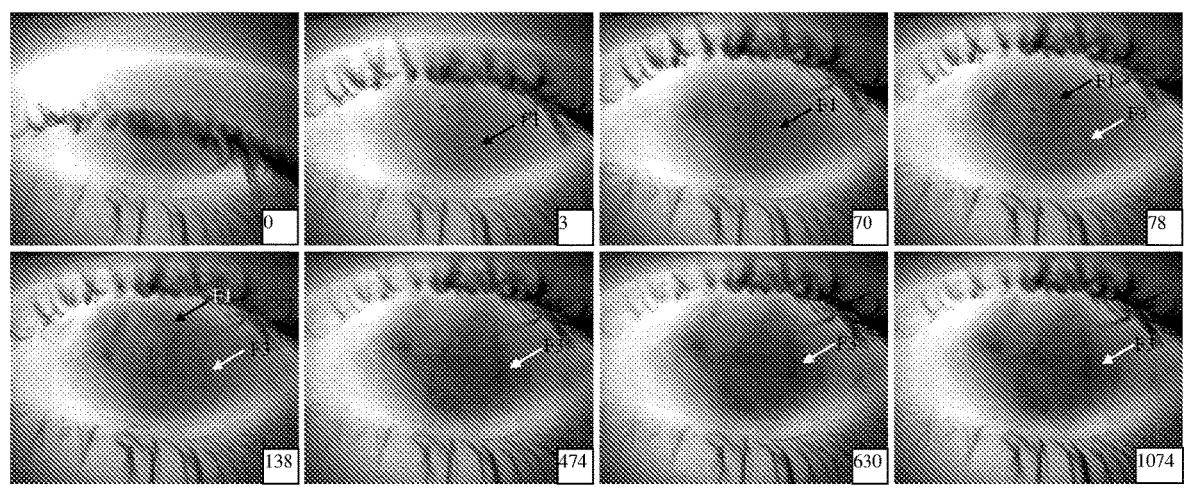
FIG. 4 shows a series of thermographs (from a thermographic movie; the numbers represent time periods of 0.01 s after the blink) of a subject's eye, who had been diagnosed with dry eye, with complete spreading, but unstable tear film following a blink.

In some subjects with abnormal tear films, the front of low thermal radiation does not reach the top of the eye, resulting in an area with low thermal radiation in those parts of the eye that the front has not moved over (FIG. 3, the low thermal radiation is attributed to enhanced evaporation in these areas).

Figure 12:
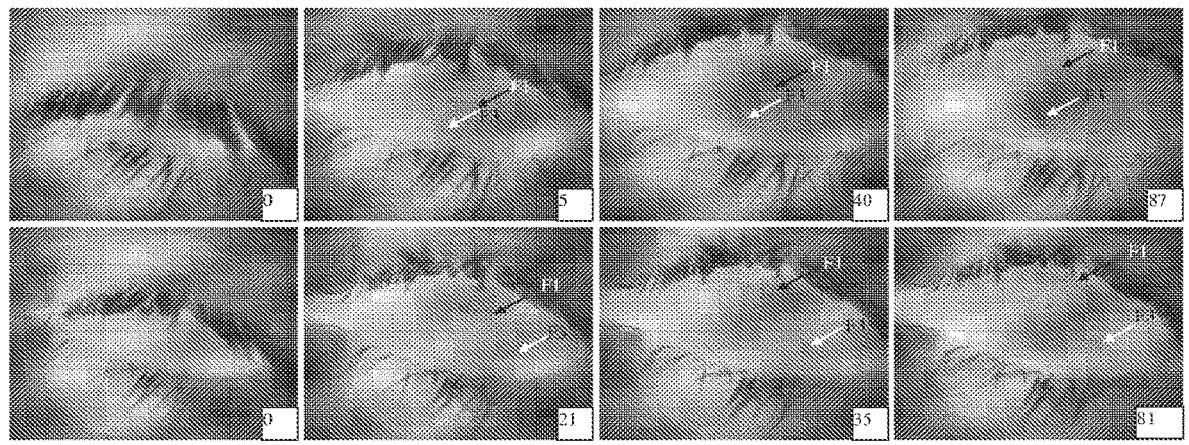
FIG. 12 shows a series of thermographs (from a thermographic movie; the numbers represent time periods of 0.01 s after the blink) of a subject's eye before and after application of a specific eye drop.

In subjects with abnormal tear films, differences in thermal radiation can be seen in the region following the front (Feature F2, the light grey region between the front and the lower lid margin in the healthy tear film). In particular, dark zones (Feature F3 in FIGS. 4, 8, 9, 10, 12, 13, 15) appearing over time on the surface of the eye represent areas of high evaporation and therefore indicative of regions where the tear film covering the eye's surface is unstable. These darkened zones (Feature F3 in FIG. 4) can appear in cases where the front has moved to the top of the eye, and in cases where the dark front does not reach the top of the eye (FIG. 12, top row).

Figure 5:
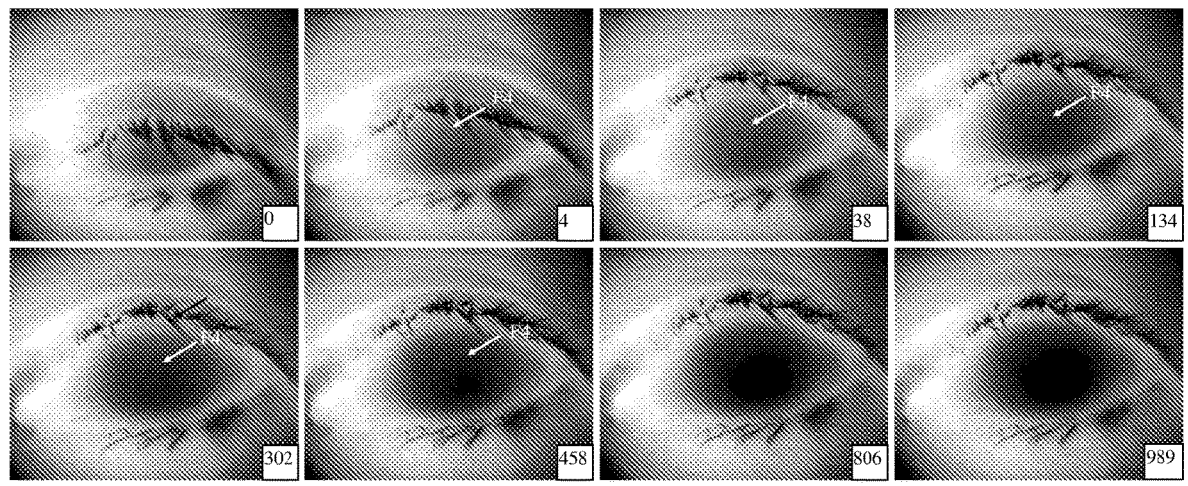
FIG. 5 shows a series of thermographs (from a thermographic movie; the numbers represent time periods of 0.01 s after the blink) of a subject's eye, who had been diagnosed with severe dry eye, with no visible spreading of a tear following a blink.
Figure 6:
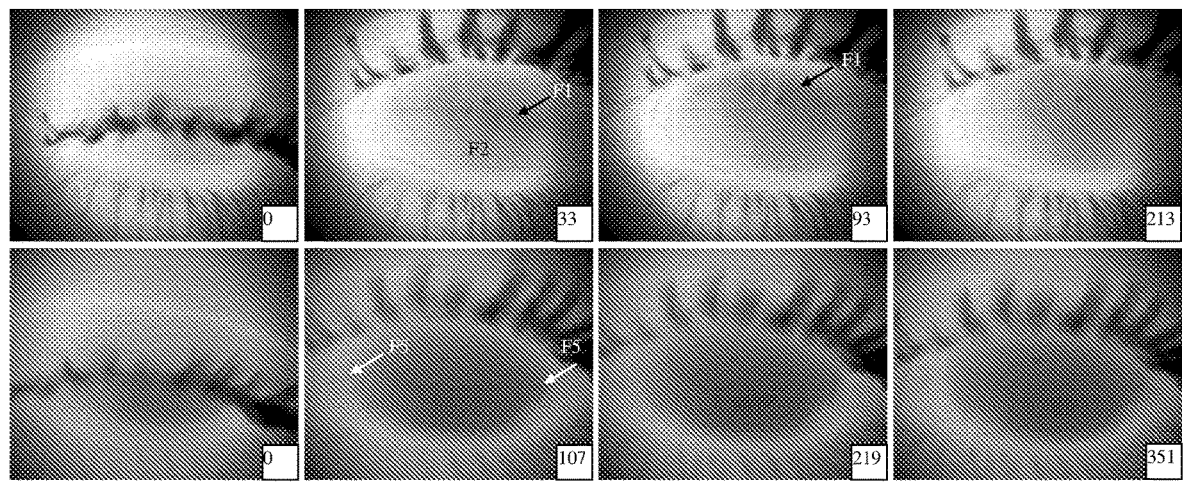
FIG. 6 shows a series of thermographs (from a thermographic movie; the numbers represent time periods of 0.01 s after the blink) after a blink before and after wearing a contact lens in a contact lens wearer.
Figure 7:
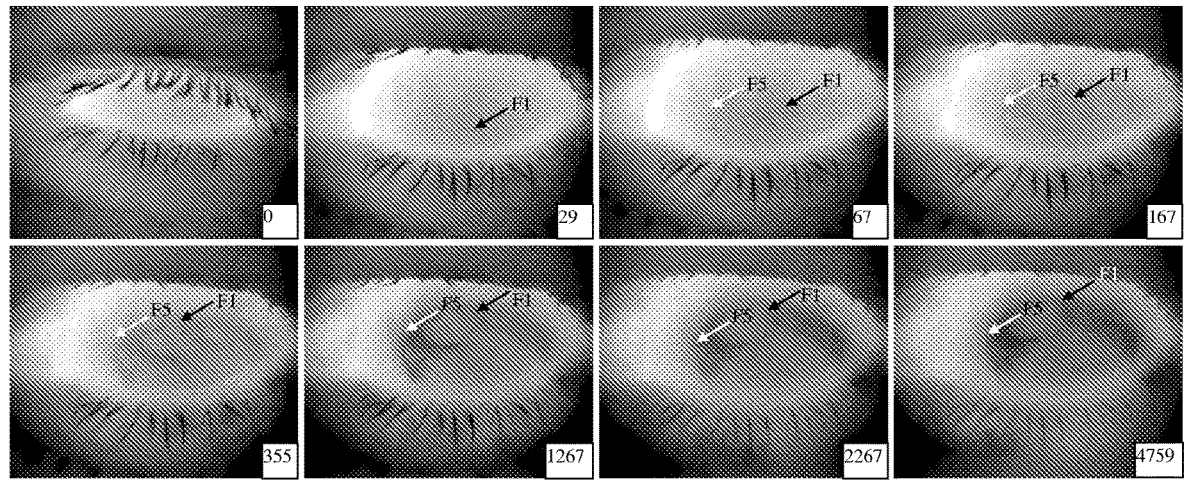
FIG. 7 shows a series of thermographs (from a thermographic movie; the numbers represent time periods of 0.01 s after the blink) after a blink showing the effect of contact lens in a naïve wearer.
Figure 8:
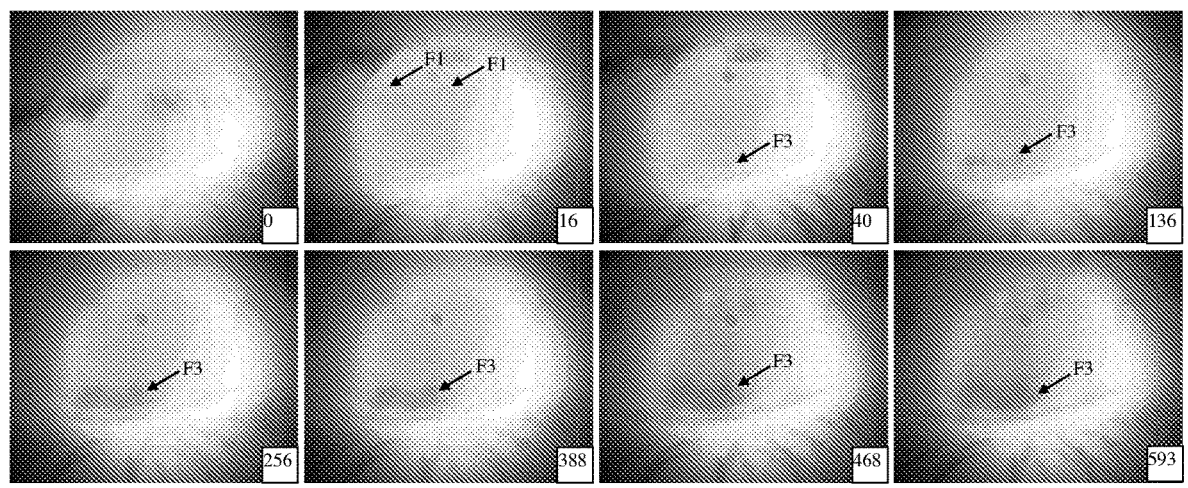
FIG. 8 shows a series of thermographs (from a thermographic movie; the numbers represent time periods of 0.01 s after the blink) of a subject's eye with Sjögren's syndrome after a blink.
Figure 9:
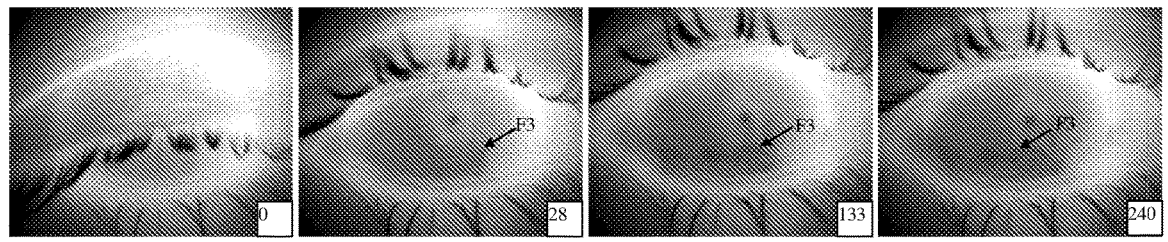
FIG. 9 shows a series of thermographs (from a thermographic movie; the numbers represent time periods of 0.01 s after the blink) of a subject's eye after a shingles infection.
Figure 10:
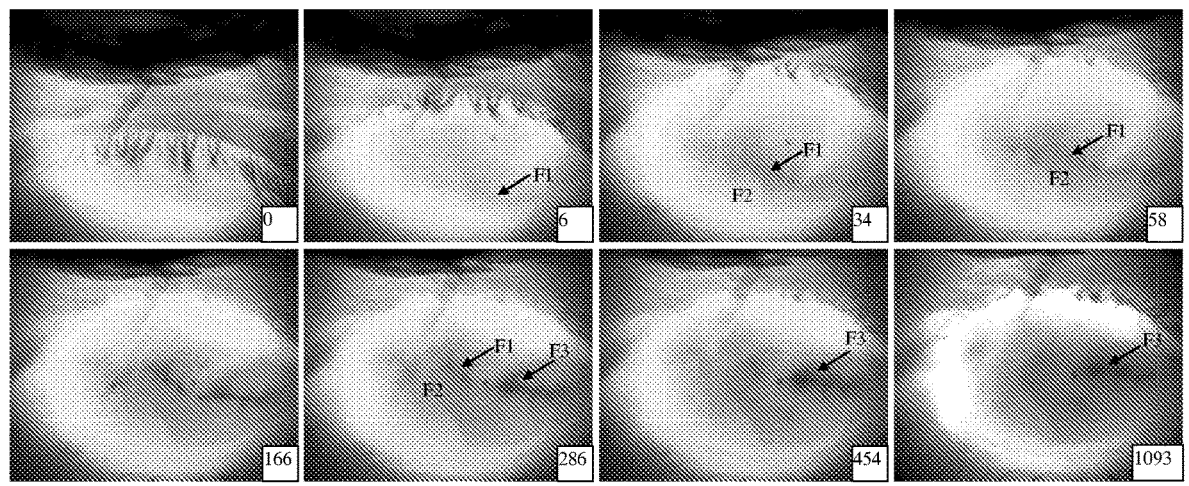
FIG. 10 shows a series of thermographs (from a thermographic movie; the numbers represent time periods of 0.01 s after the blink) of a subject's eye having a corneal lesion.

In some cases of subjects with an abnormal tear film, no zone can be seen moving over the eye, but instead there is a rapid decrease in thermal radiation of the ocular surface due to excessive evaporation (FIG. 5). Extensive research has shown that for the spreading front (Feature F1) to be seen, the aqueous part of the tear film together with the tear film lipids released from the meibomian glands have to interact with mucinious components of the tear film. A tear film devoid of the front (Feature F1) as seen in FIG. 5 as an example is indicative of an abnormal interaction in this respect.

The interaction of the aqueous and lipid components with mucin components of the tear film indeed slows down the tear film spreading over the eye to the extent that it becomes visible with the method disclosed in this invention. Thus, in a diseased state of the eye as seen in FIG. 5, the spread is too fast to be registered and the overall differential in emissivity with regard to the lipid layer and in thermal radiation with regard to evaporation is too low to be registered. An aqueous layer still covers the eye's surface directly after the blink as seen in the reflecting of the image of the infrared camera (Feature F4 in FIG. 5) in the thermographs. In cases as shown here in FIG. 5, where the tear film shows excessive evaporation, this image disappears indicating that the ocular surface has become dry (FIG. 5 at time 806).

Together, the afore mentioned scientific findings demonstrate that this invention allows observation of the dynamics of the tear film reforming while opening the eye at the end of a blink cycle, and provides visual information that allows to distinguish between subjects showing an effective and healthy spreading of the tear film, subjects having a slow spreading of the tear film, subjects having an incomplete spreading of the tear film, subjects having an impaired spreading of the tear film, subjects with no spreading of the tear film, subjects with initial spreading of the film followed by spots of areas with decreased thermal radiation in different regions of the ocular surface and subjects with other forms of abnormal stability of the tear film. In addition, the invention can show the effects on the tear film of improper blink cycles or other altered blinking regimes.

The invention also allows the visualisation of tear film dynamics when an object, such as a contact lens (Feature F5 in FIGS. 6 and 7) or other ocular device is placed in the eye. Here the spreading of the tear film is severely affected.

Figure 11:
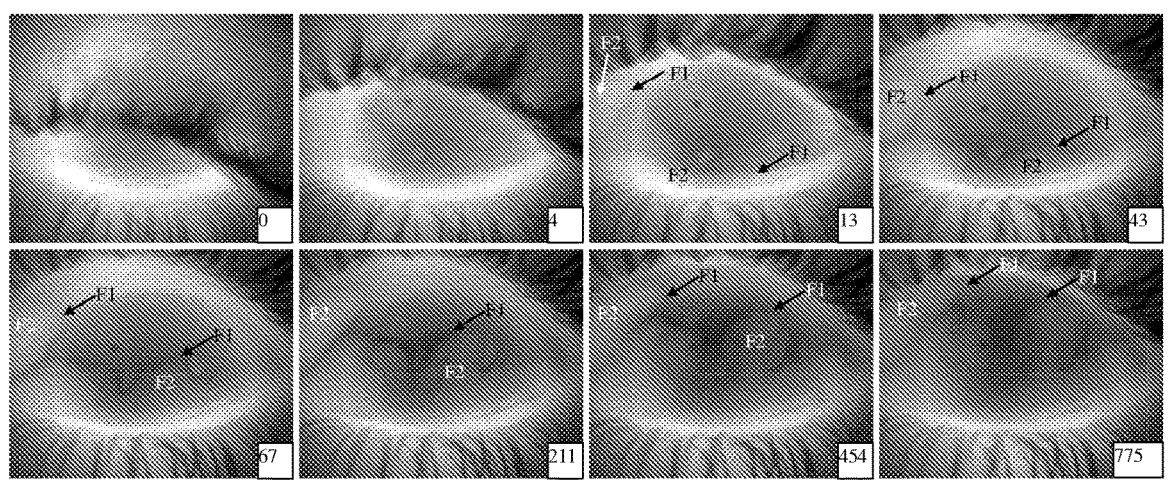
FIG. 11 shows a series of thermographs (from a thermographic movie; the numbers represent time periods of 0.01 s after the blink) of a subject's eye with keratoconus.

The technology also allows evaluation of the tear film in medical conditions, such as Sjögren's syndrome (FIG. 8) and shingles (FIG. 9), which are known to affect the tear film, and also conditions that affect the ocular surface such as corneal scarring (localised Feature F3 in FIG. 10), such as that caused by previous ocular surgery, and keratoconus (abnormal front, Feature F1 in FIG. 11, and abnormal spreading, Feature F2 in FIG. 11). The technology also allows a near or complete lack of tear film in the eye to be detected.

Figure 13:
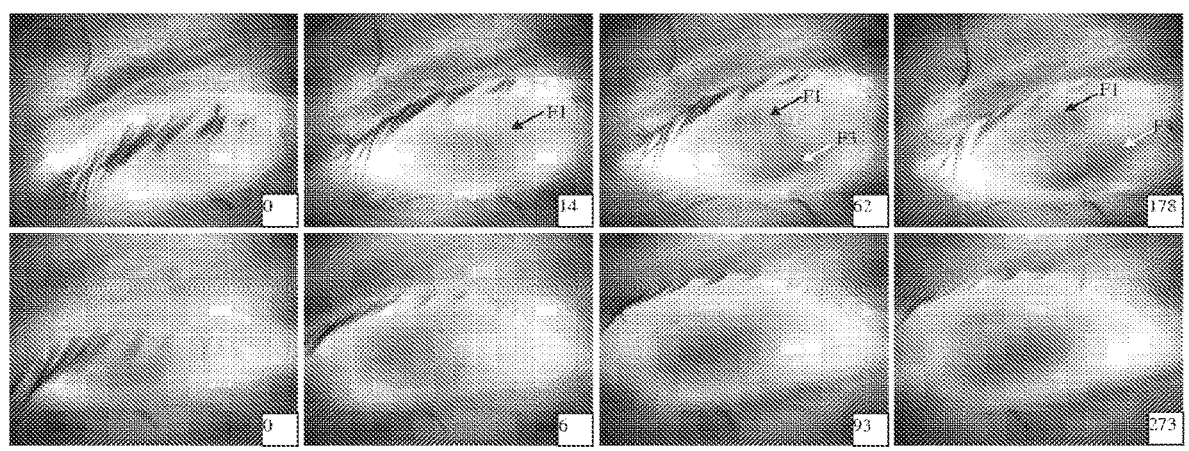
FIG. 13 shows a series of thermographs (from a thermographic movie; the numbers represent time periods of 0.01 s after the blink) of a subject's eye before and after application of another specific eye drop.

The technology also allows evaluation of the tear film dynamics before (upper row of thermographs in FIGS. 12 and 13) and after application of eye drops (lower row of FIGS. 12 and 13). Using this technique the immediate effects of the eye drop can be evaluated as well as the effects of a single dose of the eye drop or the effects of continued use of the eye drop over time. Similarly, other treatments affecting the tear film can be visualised.

Figure 14:
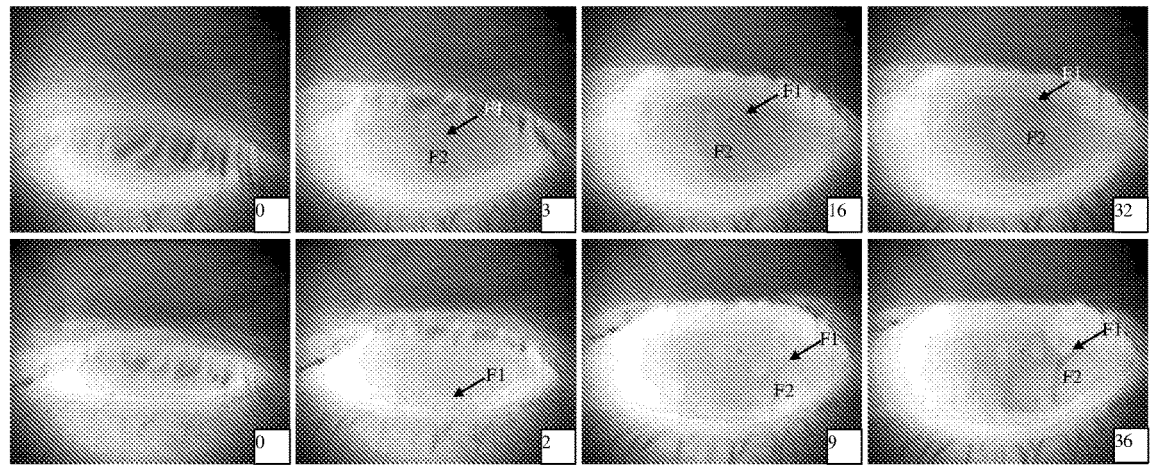
FIG. 14 shows a series of thermographs (from a thermographic movie; the numbers represent time periods of 0.01 s after the blink) of a subject's eye before and after a forceful blink.
Figure 15:
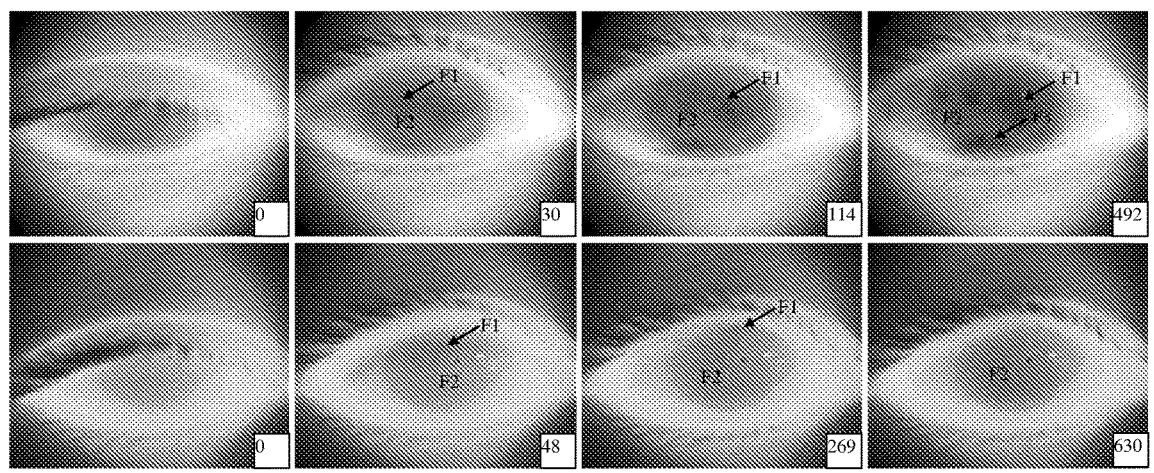
FIG. 15 shows a series of thermographs (from a thermographic movie; the numbers represent time periods of 0.01 s after the blink) of a subject's eye before and after doing eyelid blink exercises for a week.

The technology also allows evaluation of the effects of forceful blinks and blink exercises on the tear film dynamics. The upper row in FIG. 14 shows the features of a normal blink and these features are disrupted after a stronger blink (lower row FIG. 14). The upper row in FIG. 15 shows the tear film before doing blink exercises to enhance the performance of the tear film and the lower row shows the effect on the tear film after a week of blink exercises.

The invention also would allow quantitative data to be gained about the ocular temperature of a point, line or area on the ocular surface to be mapped over time. Hence, such quantitative detailed analysis of the data could be further used to evaluate the degree of change to temperature of a defined point or region on the ocular surface over time and matched with severity of tear film abnormality. However, as described in the forgoing examples due to the instantaneous and visual nature of this technology, such quantitative analyses are unnecessary in order to distinguish between a normal and abnormal natural tear film.

The herein disclosed method using a tear film thermographer can be used to visualise the tear film of subjects in real time. It will be helpful in monitoring and visualising the quality and performance of the tear film as part of judging the eye health of subjects by professionals working in ophthalmology and optometry.

Whilst the present invention has been described with reference to particular embodiments, it will be understood that many modifications will be apparent to those skilled in the art. All such variations and modifications should be considered to fall within the scope of the invention as broadly described and as claimed below.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The invention having been disclosed herein can be varied in the apparatus and setup as described here by those skilled in the art, but all such changes which might occur are within the scope of the invention, as set forth in the following claims.

The claims defining the invention are as follows:

1. An apparatus for observing a tear film on a person's or animal's eye, the apparatus comprising:
   an infrared sensitive camera that includes a camera lens system; and;
   a computer configured to receive data from the camera, process the data using software and represent the processed data on a display,
   wherein the camera is configured to measure temporal and spatial changes of thermal radiation from a surface of the eye at a frame rate, a spatial resolution, and a thermal sensitivity that allows the dynamics of the tear film to be visualised.

2. The apparatus according to claim 1, the apparatus further comprising a frame including an adjustable chin rest, wherein the camera is mounted to the frame.

3. The apparatus according to claim 1, wherein the camera is hand held.

4. The apparatus according to claim 1, wherein the dynamics of the tear film are visualised during and after a blink.

5. The apparatus according to claim 1, wherein the camera includes a detector for wavelengths in the bands from 2 micrometres to 14 micrometres.

6. The apparatus according to claim 1, wherein the camera includes a detector that captures at least 320×240 pixels.

7. The apparatus according to claim 1, wherein the camera includes a detector with a pitch resolution of 17 micrometres or less.

8. The apparatus according to claim 1, wherein the frame rate is at least 25 frames per second.

9. The apparatus according to claim 1, wherein the thermal sensitivity is at least 20 milliKelvin.

10. The apparatus according to claim 1, wherein the camera is an uncooled camera.

11. A method of observing a tear film on an eye of a person or an animal using an apparatus comprising an infrared sensitive camera that includes a camera lens system, the camera being configured to measure temporal and spatial changes of thermal radiation from a surface of the eye at a frame rate, a spatial resolution, and a thermal sensitivity that allows the dynamics of the tear film to be visualised, wherein the method includes the step of viewing the dynamics of the tear film using the apparatus.

12. The method according to claim 11, further including the step of visualising a tear film abnormality in the eye that is caused by an abnormal spreading of the tear film.

13. The method according to claim 11, further including the step of visualising a tear film abnormality in the eye that is caused by an abnormal stability of the tear film.

14. The method according to claim 11, further including the step of visualising a change to the tear film in the eye that is caused by wearing a contact lens or other ocular device.

15. The method according to claim 11, further including the step of visualising a change to the tear film in the eye that is caused by a previous ocular surgery.

16. The method according to claim 11, further including the step of visualising a change to the tear film in the eye that is caused by an altered physiological or pathological state of the eye surface.

17. The method according to claim 11, further including the step of visualising a change to the tear film in the eye that is caused by a treatment of the eye.

18. The method according to claim 11, further including the step of visualising a change to the tear film in the eye that is caused by a different blinking regime.

19. The method according to claim 11, wherein the dynamics of the tear film are viewed during and after a blink.

20. A method of viewing an eye of a person or an animal, the method including the step of:
 viewing the eye using an apparatus defined in accordance with claim 1; and,
 detecting a lack of tear film in the eye.

* * * * *